US00PP21658P2

(12) United States Plant Patent
Westhoff

(10) Patent No.: US PP21,658 P2
(45) Date of Patent: Jan. 18, 2011

(54) ***CALIBRACHOA* PLANT NAMED 'WESCAIN'**
(50) Latin Name: ***Calibrachoa* sp.**
Varietal Denomination: Wescain

(75) Inventor: Heinrich Westhoff, Südlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 0 days.

(21) Appl. No.: 12/587,457

(22) Filed: Oct. 7, 2009

(51) Int. Cl.
*A01H 5/00* (2006.01)

(52) U.S. Cl. ..... Plt./413
(58) Field of Classification Search ..... Plt./413

See application file for complete search history.

*Primary Examiner*—Kent L Bell
(74) *Attorney, Agent, or Firm*—C. A. Whealy

(57) ABSTRACT

A new and distinct cultivar of *Calibrachoa* plant named 'Wescain', characterized by its compact, semi-upright and mounding growth habit; vigorous growth habit; medium-sized oblanceolate leaves; numerous medium-sized purple violet-colored flowers; and good garden performance.

1 Drawing Sheet

Botanical designation: *Calibrachoa* sp.
Cultivar denomination: 'WESCAIN'.

BACKGROUND OF THE INVENTION

The present invention relates to a new and distinct cultivar of *Calibrachoa* plant, botanically known as *Calibrachoa* sp. and hereinafter referred to by the name 'Wescain'.

The new *Calibrachoa* plant is a product of a planned breeding program conducted by the Inventor in Südlohn, Germany. The objective of the breeding program is to create new *Calibrachoa* plants with uniform plant habit and numerous attractive flowers.

The new *Calibrachoa* plant originated from a cross-pollination made by the Inventor in April, 2004 in Südlohn, Germany of a proprietary seedling selection of *Calibrachoa* sp. identified as code number 04P301, not patented, as the female, or seed, parent with a proprietary seedling selection of *Calibrachoa* sp. identified as code number 04P932, not patented, as the male, or pollen, parent. The new *Calibrachoa* plant was discovered and selected by the Inventor as a single flowering plant within the progeny of the stated cross-pollination in a controlled environment in Südlohn, Germany in May, 2007.

Asexual reproduction of the new *Calibrachoa* plant by vegetative cuttings in a controlled environment in Südlohn, Germany since 2007 has shown that the unique features of this new *Calibrachoa* plant are stable and reproduced true to type in successive generations.

SUMMARY OF THE INVENTION

Plants of the new *Calibrachoa* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Wescain'. These characteristics in combination distinguish 'Wescain' as a new and distinct cultivar of *Calibrachoa:*

1. Compact, semi-upright and mounding growth habit.
2. Vigorous growth habit.

3. Medium-sized oblanceolate leaves.
4. Numerous medium-sized purple violet-colored flowers.
5. Good garden performance.

Plants of the new *Calibrachoa* can be compared to plants of the female parent selection. Plants of the new *Calibrachoa* differ primarily from plants of the female parent selection in the following characteristics:

1. Plants of the new *Calibrachoa* are more freely branching than plants of the female parent selection.
2. Plants of the new *Calibrachoa* have more flexible lateral branches than plants of the female parent selection.
3. Plants of the new *Calibrachoa* have smaller leaves than plants of the female parent selection.
4. Plants of the new *Calibrachoa* and the female parent selection differ in flower color as plants of the female parent selection have fuchsia-colored flowers.

Plants of the new *Calibrachoa* can be compared to plants of the male parent selection. Plants of the new *Calibrachoa* differ primarily from plants of the male parent selection in the following characteristics:

1. Plants of the new *Calibrachoa* have smaller flowers than plants of the male parent selection.
2. Plants of the new *Calibrachoa* and the male parent selection differ in flower color as plants of the male parent have a conspicuous white-colored zone near the throat.

Plants of the new *Calibrachoa* can be compared to plants of the *Calibrachoa* sp. 'Wesviolet', disclosed in U.S. Plant Pat. No. 12,584. In side-by-side comparisons conducted in Südlohn, Germany, plants of the new *Calibrachoa* differed from plants of 'Wesviolet' in the following characteristics:

1. Plants of the new *Calibrachoa* were more compact than and not as trailing as plants of 'Wesviolet'.
2. Plants of the new *Calibrachoa* had larger leaves than plants of 'Wesviolet'.
3. Plants of the new *Calibrachoa* had larger flowers than plants of 'Wesviolet'.
4. Plants of the new *Calibrachoa* and 'Wesviolet' differed in flower color as plants of 'Wesviolet' had darker-colored flowers.

Plants of the new *Calibrachoa* can be compared to plants of the *Calibrachoa* sp. 'Wescavet', not patented. In side-by-side comparisons conducted in Südlohn, Germany, plants of the new *Calibrachoa* differed from plants of 'Wescavel' in the following characteristics:

1. Plants of the new *Calibrachoa* were more compact than and not as trailing as plants of 'Wescavel'.
2. Plants of the new *Calibrachoa* were more freely branching than plants of 'Wescavel'.
3. Plants of the new *Calibrachoa* had smaller leaves than plants of 'Wescavel'.
4. Plants of the new *Calibrachoa* and 'Wescavel' differed in flower color as plants of 'Wescavel' had darker-colored flowers.

BRIEF DESCRIPTION OF THE PHOTOGRAPH

The accompanying colored photograph illustrates the overall appearance of the new *Calibrachoa* plant, showing the colors as true as it is reasonably possible to obtain in colored reproductions of this type. Colors in the photograph may differ slightly from the color values cited in the detailed botanical description which accurately describe the colors of the new *Calibrachoa* plant. The photograph comprises a close-up view of a typical flowering plant of 'Wescain'.

DETAILED BOTANICAL DESCRIPTION

The aforementioned photograph and following observations, measurements and values describe plants grown in 12-cm containers in Südlohn, Germany, under commercial practice during the summer in a glass-covered greenhouse with day temperatures ranging from 20° C. to 25° C., night temperatures ranging from 16° C. to 18° C. and light levels ranging from 3 to 50 klux. Plants were 30 weeks old when the photograph and description were taken. In the following description, color references are made to The Royal Horticultural Society Colour Chart, 2001 Edition, except where general terms of ordinary dictionary significance are used.

Botanical classification: *Calibrachoa* sp. 'Wescain'.

Parentage:

*Female, or seed, parent.*—Proprietary seedling selection of *Calibrachoa* sp. identified as code number 04P301, not patented.

*Male, or pollen, parent.*—Proprietary seedling selection of *Calibrachoa* sp. identified as code number 04P932, not patented.

Propagation:

*Type.*—By vegetative cuttings.

*Time to initiate roots, summer.*—About 10 to 14 days at temperatures of 20° C.

*Time to initiate roots, winter.*—About 16 to 18 days at temperatures of 20° C.

*Time to produce a rooted young plant, summer.*—About 21 to 24 days at temperatures of 20° C.

*Time to produce a rooted young plant, winter.*—About 24 to 26 days at temperatures of 20° C.

*Root description.*—Fibrous, medium in thickness; color, close to 158A.

*Rooting habit.*—Freely branching; moderately dense to dense.

Plant description:

*Plant and growth habit.*—Compact, semi-upright and mounding plant habit; with development, plants become roughly spherical in shape; freely branching habit with lateral branches potentially developing at every node; vigorous growth habit.

*Plant height.*—About 14 cm.

*Plant diameter.*—About 37 cm to 60 cm.

Lateral branch description:

*Length.*—About 16.3 cm.

*Diameter.*—About 1.2 mm to 3 mm.

*Internode length.*—About 1 cm.

*Strength.*—Strong; flexible.

*Aspect.*—Initially upright to outwardly spreading.

*Texture.*—Pubescent.

*Color.*—Close to 146C.

Foliage description:

*Arrangement.*—Alternate, simple; sessile.

*Length.*—About 3 cm.

*Width.*—About 1 cm.

*Shape.*—Oblanceolate.

*Apex.*—Obtuse.

*Base.*—Attenuate.

*Margin.*—Entire.

*Texture, upper and lower surfaces.*—Pubescent.

*Venation pattern.*—Pinnate; arcuate.

*Color.*—Developing leaves, upper surface: Close to 146A. Developing leaves, lower surface: Close to 146B. Fully expanded leaves, upper surface: Close to 147A; venation, slightly lighter than 147A. Fully expanded leaves, lower surface: Close to 147B; venation, slightly lighter than 147B.

Flower description:

*Flower arrangement and habit.*—Single salverform flowers arising from leaf axils; freely flowering habit with usually about 28 to 44 flowers and flower buds per lateral branch; flowers face mostly outwardly.

*Fragrance.*—None detected.

*Natural flowering season.*—Plants of the new *Calibrachoa* initiate and develop flowers about 12 to 14 weeks after planting; plants flower continuously from April to October in Germany.

*Flower longevity.*—Individual flowers last about five to seven days on the plant; flowers not persistent.

*Flower diameter.*—About 3.3 cm.

*Flower length (height).*—About 2.5 cm to 3.2 cm.

*Flower throat diameter.*—About 9 mm.

*Flower tube diameter, base.*—About 4 mm.

*Flower tube length.*—About 1.6 cm.

*Flower bud.*—Shape: Oblong. Length: About 2.2 cm. Diameter: About 4.3 mm. Color: Base and mid-section, close to 145B to 145C; towards the apex, close to 83A to 83B.

*Corolla.*—Arrangement: Five petals fused at the base and opening into a flared trumpet. Petal length from throat: About 1.4 cm. Petal lobe width: About 1.6 cm. Petal shape: Roughly obovate. Petal apex: Emarginate. Petal margin: Entire. Petal texture, upper and lower surfaces: Smooth, glabrous; satiny. Color: Petal lobe, when opening, upper surface: Darker than N82A. Petal lobe, when opening, lower surface: Close to N82C. Petal lobe, fully opened, upper surface: Close to N82A; with development, color becoming closer to N82B; venation, close to 83A. Petal lobe, fully opened, lower surface: Close to N82D; with development, color becoming closer to 85C; venation, close to 152A to 152C. Throat: Close to 6B to 6C; venation, close to N77A. Tube: Close to 154C; venation, close to N77A.

*Calyx.*—Arrangement: One star-shaped calyx tube with five sepals fused at the base per flower. Sepal length: About 1.1 cm to 1.3 cm. Sepal width: About 3 mm.

Sepal shape: Lanceolate. Sepal apex: Acute. Sepal margin: Entire. Sepal texture, upper and lower surfaces: Pubescent. Color, upper and lower surfaces: Close to 146A.

*Peduncles.*—Length: About 1.7 cm. Diameter: About 0.9 mm. Strength: Moderately strong; flexible. Texture: Pubescent. Color: Close to 144A slightly tinted with close to 166A to 166B.

*Reproductive organs.*—Stamens: Quantity/arrangement: About five per flower. Filament length: About 4 mm to 6 mm. Filament color: Close to 145C. Anther shape: Ovate, four-parted. Anther length: About 1.5 mm. Anther width: About 1.5 mm. Anther color: Close to 11B. Pollen amount: Moderate. Pollen color: Close to 11B. Pistils: Quantity: One per flower. Pistil length: About 9 mm. Style length: About 7 mm. Style color: Close to 144C to 144D. Stigma shape: Ovate. Stigma color: Close to144A. Ovary color: Close to 144C. Seeds/fruits: Seed and fruit development have not been observed on plants of the new *Calibrachoa.*

Garden performance: Plants of the new *Calibrachoa* have been observed to have good garden performance and tolerate wind, rain and temperatures ranging from about 5° C. to 30° C.

Pathogen/pest resistance: Plants of the new *Calibrachoa* have not been observed to be resistant to pathogens and pests common to *Calibrachoa.*

It is claimed:

1. A new and distinct *Calibrachoa* plant named 'Wescain' as illustrated and described.

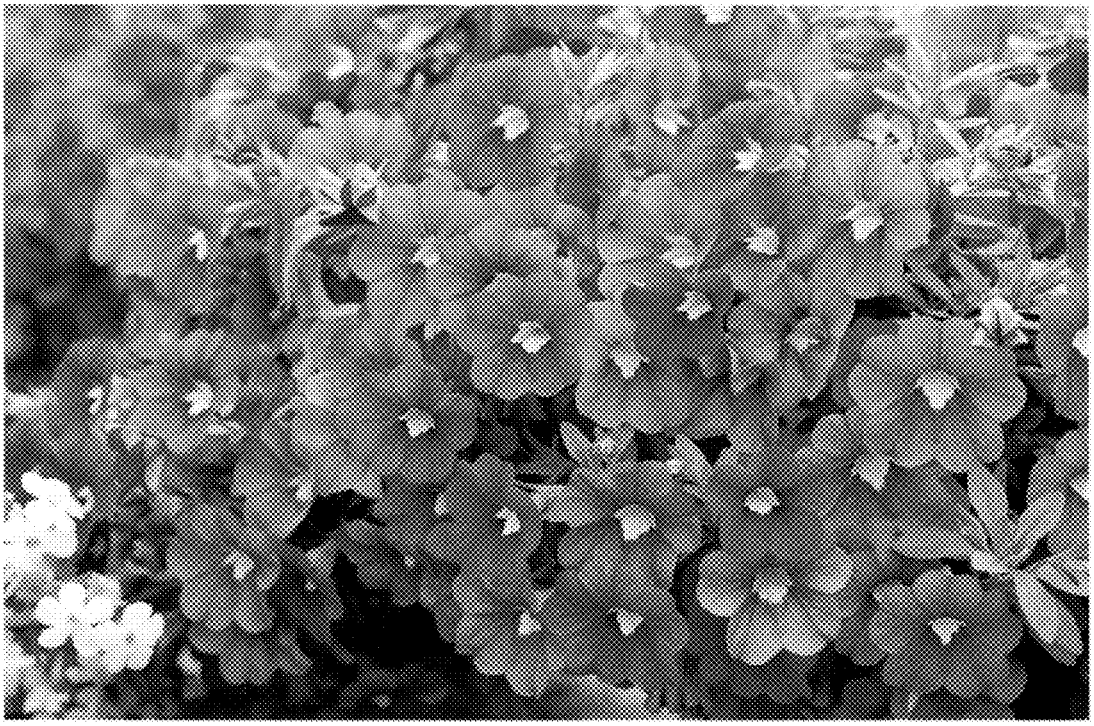

* * * * *